United States Patent [19]
Huser et al.

[11] Patent Number: 5,856,555
[45] Date of Patent: Jan. 5, 1999

[54] PROCESS FOR THE HYDROCYANATION OF ORGANIC COMPOUNDS CONTAINING ETHYLENIC UNSATURATION

[75] Inventors: Marc Huser, Villeurbanne; Robert Perron, Charly, both of France

[73] Assignee: Rhone-Poulenc Fiber & Resin Intermediates, Courbevoie Cedex, France

[21] Appl. No.: 832,689

[22] Filed: Apr. 11, 1997

Related U.S. Application Data

[63] Continuation of PCT/FR96/01509 Sep. 29, 1996.

[60] Provisional application No. 60/015,480 Apr. 12, 1996.

[30] Foreign Application Priority Data

Sep. 29, 1995 [FR] France ................................. 95 11689

[51] Int. Cl.$^6$ ................................................. C07C 253/00
[52] U.S. Cl. .......................................................... 558/338
[58] Field of Search ............................................. 558/338

[56] References Cited

U.S. PATENT DOCUMENTS

| | | | |
|---|---|---|---|
| 4,087,452 | 5/1978 | Kuntz ........................................ | 260/464 |
| 4,874,884 | 10/1989 | McKinney et al. ....................... | 558/338 |
| 5,175,335 | 12/1992 | Casalnuovo et al. .................... | 558/338 |

FOREIGN PATENT DOCUMENTS

| | | |
|---|---|---|
| 0 133 127 | 2/1985 | European Pat. Off. . |
| 0 647 619 | 4/1995 | European Pat. Off. . |
| 0 650 959 | 5/1995 | European Pat. Off. . |
| 2033107 | 11/1970 | France . |
| 2 069 411 | 9/1971 | France . |
| 2 338 253 | 8/1977 | France . |
| 95/22405 | 8/1995 | WIPO . |
| 95/30680 | 11/1995 | WIPO . |

*Primary Examiner*—Johann Richter
*Assistant Examiner*—Joseph Murray
*Attorney, Agent, or Firm*—Burns, Doane, Swecker & Mathis, L.L.P.

[57] ABSTRACT

The present invention relates to a process for the hydrocyanation of organic compounds containing ethylenic unsaturation to nitrites, in particular the hydrocyanation of diolefins or of substituted olefins, such as alkenenitriles.

More specifically, it comprises a process for the hydrocyanation of organic compounds containing at least one ethylenic double bond by reaction with hydrogen cyanide in the presence of an aqueous solution of a catalyst comprising at least one transition metal compound and at least one water-soluble phosphine, characterized in that the said water-soluble phosphine is a monodentate or bidentate phosphine.

21 Claims, No Drawings

PROCESS FOR THE HYDROCYANATION OF ORGANIC COMPOUNDS CONTAINING ETHYLENIC UNSATURATION

CROSS-REFERENCE TO RELATED APPLICATIONS

This application is a continuation of International Patent Application No. PCT/FR96/01509, and filed Sep. 27, 1996, and designating the United States, and also claims priority of U.S. Provisional application Ser. No. 60/015,480, filed Apr. 12, 1996.

BACKGROUND OF THE INVENTION

1. Technical Field of the Invention

The present invention relates to a process for the hydrocyanation of organic compounds containing ethylenic unsaturation to nitriles, in particular the hydrocyanation of diolefins or of substituted olefis, such as alkenenitriles.

2. Description of the Prior Art

French Patent No. 1,599,761 describes a process for the preparation of nitrites by addition of hydrocyanic acid to organic compounds having at least one ethylenic double bond in the presence of a nickel catalyst and of a triaryl phosphite. This reaction can be carried out in the presence or in the absence of a solvent.

When a solvent is used in this process of the prior art, it is preferably a hydrocarbon, such as benzene or xylenes, or a nitrile, such as acetonitrile.

The catalyst used in an organic nickel complex containing ligands, such as phosphines, arsines, stibines, phosphites, arsenites or antimonites.

The presence of a promoter to activate the catalyst, such as a boron compound or a metal salt, generally a Lewis acid, is also recommended in the patent.

In this process, the medium is entirely organic and one of its major disadvantages is the difficulty in separating, at the end of a reaction, the hydrocyanation products from the catalytic solution containing a number of constituents (nickel complex, triaryl phosphite, promoter), for the purpose in particular of recycling the latter solution in a new hydrocyanation reaction. Such a separation is problematic, very complex and incomplete and a substantial loss of catalyst is observed, as well as the presence of the said catalyst in the hydrocyanation products. This loss of metal catalyst, generally based on nickel, poses economic problems but raises, in an even more pressing way, questions regarding the future of such metals, because the discharge of effluents or the storage of waste are environmentally less and less acceptable.

Provision has been made, in Patent FR-A-2,338,253, for carrying out the hydrocyanation of compounds having at least one ethylenic unsaturation in the presence of an aqueous solution of a compound of a transition metal, in particular nickel, palladium or iron, and of a sulphonated phosphine.

The sulphonated phosphines described in this patent are sulphonated triarylphosphines and more particularly sulphonated triphenylphosphines.

This process makes possible good hydrocyanation, in particular of butadiene and pentenenitriles, and an easy separation of the catalytic solution by simple separation by settling and consequently avoids as far as possible the discharge of effluents or of waste containing the metals acting as catalysts.

The results obtained during the hydrocyanation reaction are relatively good with various substrates and in particular with functionalized olefins such as pentenenitriles. However, it turns out that the lifetime of the catalyst could be improved in order to allow this type of process to be operated industrially.

The present invention relates to a process capable of providing an outstanding industrial solution to this very important hydrocyanation reaction which results, when it is applied, for example, to butadiene and then to pentenenitriles, in adiponitrile, one of the base compounds necessary for the manufacture of polyamide-6,6.

More specifically, it comprises a process for the hydrocyanation of organic compounds containing at least one ethylenic double bond by reaction with hydrogen cyanide in the presence of an aqueous solution of a catalyst comprising at least one compound of a transition metal and at least one water-soluble phosphine, characterized in that the said water-soluble phosphine is a monodentate or bidentate phosphine corresponding to the general formula (I):

in which:

Ar1 and Ar2, which are identical or different, represent aryl groups or aryl groups containing one or a number of substituents such as:

alkyl or alkoxy radical having 1 to 4 carbon atoms, halogen atom, hydrophilic group, such as:

—COOM, —SO$_3$M or —PO$_3$M, M representing an inorganic or organic cationic residue chosen from the proton, cations derived from alkali or alkaline-earth metals, ammonium cations —N(R)$_4$ in the formula of which the R symbols, which are identical or different, represent a hydrogen atom or an alkyl radical having from 1 to 4 carbon atoms, and other cations derived from metals, the arylcarboxylic acid, arylsulphonic acid or arylphosphonic acid salts of which are soluble in water, —N(R)$_3$, in the formula of which the R symbols, which are identical or different, represent a hydrogen atom or an alkyl radical having from 1 to 4 carbon atoms,

—OH

Ar3 represents an aryl group containing one or a number of substituents, such as:

alkyl or alkoxy radical having 1 to 4 carbon atoms, halogen atom, hydrophilic group, such as:

—COOM or —PO$_3$M, M representing an inorganic or organic cationic residue chosen from the proton, cations derived from alkali or alkaline-earth metals, ammonium cations —N(R)$_4$, in the formula of which the R symbols, which are identical or different, represent a hydrogen atom or an alkyl radical having from 1 to 4 carbon atoms, and other cations derived from metals, the arylcarboxylic acid or arylphosphonic acid salts of which are soluble in water, —N(R)$_3$, in the formula of which the R symbols, which are identical or different, represent a hydrogen atom or an alkyl radical having from 1 to 4 carbon atoms, —OH,
at least one of the said substituents of Ar3 being a hydrophilic group as defined above,
a represents 0 or 1,
b represents 0 or 1,
c represents an integer from 0 to 3,
D represents an alkyl group, a cycloalkyl group or an alkyl or cycloalkyl group containing one or a number of substituents, such as:
  alkoxy radical having 1 to 4 carbon atoms,
  halogen atom,
  hydrophilic group, such as:
    —COOM, —SO$_3$M or —PO$_3$M, M representing an inorganic or organic cationic residue chosen from the proton, cations derived from alkali or alkaline-earth metals, ammonium cations —N(R)$_4$, in the formula of which the R symbols, which are identical or different, represent a hydrogen atom or an alkyl radical having from 1 to 4 carbon atoms, and other cations derived from metals, the arylcarboxylic acid, arylsulphonic acid or arylphosphonic acid salts of which are soluble in water,
    —N(R)$_3$, in the formula of which the R symbols, which are identical or different, represent a hydrogen atom or an alkyl radical having from 1 to 4 carbon atoms,
    —OH
d represents an integer from 0 to 3,
the sum (a+b+c+d) is equal to 3
or to the general formula (II):

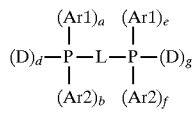

in which:
Ar1, Ar2 and D have the meanings indicated above for the formula (I),
a, b, e and f each represent 0 or 1,
d and g each represent an integer from 0 to 2,
the sum (a+b+d) is equal to 2,
the sum (e+f+g) is equal to 2,
L represents a single valency bond or a divalent hydrocarbon radical, such as an alkylene radical, a cycloalkylene radical, an arylene radical or a radical deriving from a heterocycle containing one or two oxygen, nitrogen or sulphur atoms in the ring, these various cyclic radicals being bonded directly to one of the phosphorus atoms or to both phosphorus atoms or being bonded to one of the phosphorus atoms or to both via a linear or branched alkylene radical having from 1 to 4 carbon atoms, it being possible for the ring or rings which are optionally part of the divalent radical L to contain one or a number of substituents, such as an alkyl group having 1 to 4 carbon atoms.
Mention may be made, as examples of metals, the arylcarboxylic acid, arylsulphonic acid or arylphosphonic acid salts of which are soluble in water, of lead, zinc and tin.
The expression soluble in water is understood to mean, in the present text, a compound soluble to at least 0.01 g per liter of water.
The preferred water-soluble phosphines are the phosphines of formula (I) or of formula (II) in which Ar1 and Ar2 are phenyl groups or phenyl groups containing one or two substituents as defined above, Ar3 is a phenyl group containing one or two substituents as defined above, D is an alkyl group having from 1 to 6 carbon atoms, a cycloalkyl group having 5 to 8 carbon atoms, an alkyl group having from 1 to 6 carbon atoms containing one or a number of substituents as defined above or a cycloalkyl group having 5 to 8 carbon atoms containing one or a number of substituents as defined above and L is a single valency bond, an alkylene radical having from 1 to 6 carbon atoms, a monocyclic or bicyclic cycloalkylene radical having from 4 to 12 carbon atoms, a phenylene radical, a diphenylene radical, a naphthylene radical, a dinaphthylene radical or a radical deriving from a heterocycle containing one or two oxygen, nitrogen or sulphur atoms in the ring, these various cyclic radicals being bonded directly to one of the phosphorus atoms or to both phosphorus atoms or being bonded to one of the phosphorus atoms or to both via a linear or branched alkylene radical having from 1 to 4 carbon atoms, it being possible for the ring or rings which are optionally part of the divalent radical L to contain one or a number of substituents, such as an alkyl group having 1 to 4 carbon atoms.
The preferred water-soluble phosphines are the phosphines of formula (I) or of formula (II) in which:
the substituent or substituents of Ar1 and Ar2, which are identical or different, represent groups such as:
  alkyl or alkoxy radical having 1 to 2 carbon atoms,
  chlorine atom,
  hydrophilic group, such as:
    —COOM, —SO$_3$M or —PO$_3$M, M representing an inorganic or organic cationic residue chosen from the proton, cations derived from sodium, potassium, calcium or barium, ammonium, tetramethylammonium, tetraethylammonium, tetrapropylammonium or tetrabutylammonium cations and cations derived from zinc, lead or tin,
    —N(R)$_3$, in the formula of which the R symbols, which are identical or different, represent a hydrogen atom or an alkyl radical having from 1 to 4 carbon atoms,
    —OH
the substituent or substituents of Ar3, which are identical or different, represent groups such as:
  alkyl or alkoxy radical having 1 to 2 carbon atoms,
  chlorine atom,
  hydrophilic group, such as:
    —COOM or —PO$_3$M, M representing an inorganic or organic cationic residue chosen from the proton, cations derived from sodium, potassium, calcium or barium, ammonium, tetramethylammonium, tetraethylammonium, tetrapropylammonium or tetrabutylammonium cations and cations derived from zinc, lead or tin,
    —N(R)$_3$, in the formula of which the R symbols, which are identical or different, represent a hydrogen atom or an alkyl radical having from 1 to 4 carbon atoms,
    —OH
overall at least two of the said substituents of Ar1, Ar2, Ar3 and D, for the phosphines of formula (I), and of Ar1, Ar2 and D, for the phosphines of formula (II), being a hydrophilic group as defined above.
Mention may be made, as non-limiting examples of phosphines of general formula (I), of in particular tris(hydroxymethyl)phosphine, tris(2-hydroxyethyl)phosphine, tris(3-hydroxypropyl)phosphine, tris(2-carboxymethyl)phosphine, the sodium salt of tris(3-carboxyphenyl)phosphine, tris(3-carboxyethyl)phosphine, the iodide of tris(4-trimethylammoniophenyl)phosphine, the sodium salt of tris(2-phosphonatoethyl)phosphine, bis(2-carboxyethyl) phenylphosphine, the sodium salt of tris(para-phosphophenyl)phosphine, the sodium salt of bis(meta-sulphophenyl)(para-carboxyphenyl)phosphine or the sodium salt of bis(meta-sulphophenyl)(2-sulphoethyl) phosphine.

Mention may be made, as non-limiting examples of phosphines of general formula (II), of in particular the sodium salt of 2,2'-bis[di(sulphonatophenyl)phosphino]-1,1'-binaphthyl, the sodium salt of 1,2-bis-[di(sulphonatophenyl)phosphinomethyl]cyclobutane (CBDTS), 1,2-bis(dihydroxymethylphosphino)ethane, 1,3-bis(dihydroxymethylphosphino)propane or the sodium salt of 2,2'-bis[di(sulphonatophenyl)phosphinomethyl]-1,1'-binaphthyl.

Some of the water-soluble phosphines of formula (I) or (II) are commercially available.

For the preparation of the others, reference may be made to the general or specific processes for the synthesis of phosphines described in the general literature, such as Houben-Weyl, Methoden der organischen Chemie [Methods of Organic Chemistry], organische Phosphor Verbindungen [Organic Phosphorus Compounds], Part 1 (1963).

Finally, for the preparation of undescribed water-soluble derivatives, it is possible, starting with phosphines not containing water-soluble substituents defined above, to introduce one or a number of these hydrophilic substituents. Thus, sulphonate groups for example can be introduced by the reaction of $SO_3$ in sulphuric acid. Carboxylate, phosphonate and quaternary ammonium groups can likewise be introduced by applying the chemical methods known for this type of synthesis.

Compounds of nickel, of palladium and of iron are preferably used as transition metal compounds. Compounds which are soluble in water or capable of dissolving under the reactions conditions are used. The residue bonded to the metal is not critical, as long as it satisfies these conditions.

Among the abovementioned compounds, the most preferred compounds are those of nickel and mention may be made, as non-limiting examples, of:

compounds in which the nickel is in the zero oxidation state, such as potassium tetracyanonickelate $K_4[Ni(CN)_4]$, bis(acrylonitrile)nickel(O), bis(1,5-cyclooctadiene)nickel and derivatives containing ligands from group Va, such as tetrakis (triphenylphosphine)nickel(O) (in the latter case, the compound can be dissolved in a water-immiscible solvent, such as toluene, and then an aqueous solution of sulphonated phosphine extracts part of the nickel, a red coloration developing in the aqueous solution which separates by settling);

nickel compounds such as carboxylates (in particular the acetate), carbonate, bicarbonate, borate, bromide, chloride, citrate, thiocyanate, cyanide, formate, hydroxide, hydrophosphite, phosphite, phosphate and derivatives, iodide, nitrate, sulphate, sulphite, arylsulphonates and alkylsulphonates.

It is not necessary for the nickel compound itself to be soluble in water. For example, nickel cyanide, which is sparingly soluble in water, is very soluble in an aqueous solution of phosphine.

When the nickel compound used corresponds to a nickel oxidation state greater than zero, a nickel-reducing agent which reacts preferentially with nickel under the reaction conditions is added to the reaction mixture. This reducing agent can be organic or inorganic. Mention may be made, as non-limiting examples, of $NaBH_4$, Zn powder, magnesium, $KBH_4$ and borohydrides which are preferably soluble in water.

This reducing agent is added in an amount such that the number of redox equivalents is between 1 and 10. However, values of less than 1 and greater than 10 are not excluded.

When the nickel compound used corresponds to the 0 nickel oxidation state, it is also possible to add a reducing agent of the type of those mentioned above, but this addition is not essential.

When an iron compound is used, the same reducing agents are suitable.

In the case of palladium, the reducing agents can additionally be components of the reaction mixture (phosphine, solvent, olefin).

The organic compounds containing at least one ethylenic double bond which are more particularly employed in the present process are diolefins, such as butadiene, isoprene, 1,5-hexadiene or 1,5-cyclooctadiene, aliphatic nitriles containing ethylenic unsaturation, particularly linear pentenenitriles, such as 3-pentenenitrile or 4-pentenenitrile, monoolefins, such as styrene, methylstyrene, vinylnaphthalene, cyclohexene or methylcyclohexene, and mixtures of a number of these compounds.

The pentenenitriles in particular can contain amounts, generally minor, of other compounds, such as 2-methyl-3-butenenitrile, 2-methyl-2-butenenitrile, 2-pentenenitrile, valeronitrile, adiponitrile, 2-methylglutaronitrile, 2-ethylsuccinonitrile or butadiene, originating, for example, from the prior hydrocyanation reaction of butadiene.

Not insignificant amounts of 2-methyl-3-butenenitrile and 2-methyl-2-butenenitrile are formed, with the linear pentenenitriles, during the hydrocyanation of butadiene.

The catalytic solution used for the hydrocyanation according to the process of the invention can be prepared before it is introduced into the reaction region, for example by addition, to the aqueous solution of the water-soluble phosphine of formula (I) or (II), of the appropriate amount of chosen transition metal compound and optionally of the reducing agent. It is also possible to prepare the catalytic solution "in situ" by simple mixing of these various constituents.

The amount of nickel compound or compound of another transition metal used is chosen so that there is, per liter of reaction solution, between $10^{-4}$ and 1, and preferably between 0.005 and 0.5, mol of nickel or of the other transition metal employed.

The amount of water-soluble phosphine of formula (I) or (II) used to prepare the reaction solution is chosen so that the number of moles of this compound with respect to 1 mol of transition metal is from 0.5 to 2000 and preferably from 2 to 300.

Although the reaction is generally carried out without a third solvent, it can be advantageous to add an inert water-immiscible organic solvent which can be that of the subsequent extraction.

Mention may be made, as examples of such solvents, of aromatic, aliphatic or cycloaliphatic hydrocarbons which maintain the reaction mixture in the two-phase state.

Thus, once the reaction has ended, it is very easy to separate, on the one hand, an aqueous phase containing the water-soluble phosphine or phosphines of formula (I) or (II) and the transition metal compound and, on the other hand, an organic phase composed of the reactants involved in the reaction, the reaction products and, if appropriate, the water-immiscible organic solvent.

The hydrocyanation reaction is generally carried out at a temperature from 10° C. to 200° C. and preferably from 30° C. to 120° C.

The process of the invention can be carried out continuously or batchwise.

The hydrogen cyanide employed can be prepared from metal cyanides, in particular sodium cyanide, or from cyanohydrins.

The hydrogen cyanide is introduced into the reactor in the gaseous form or in the liquid form. It can also be dissolved beforehand in an organic solvent.

Within the context of a batchwise implementation, it is possible, in practice, to charge to a reactor which has been purged beforehand using an inert gas (such as nitrogen or argon) either an aqueous solution containing all or part of the various constituents, such as the water-soluble phosphine, the transition metal compound, the possible reducing agent and the possible solvent, or the said constituents separately. Generally, the reactor is then brought to the chosen temperature and then the pentenenitrile is introduced. The hydrogen cyanide is then itself introduced, preferably continuously and uniformly.

When the reaction (the progress of which can be monitored by quantitative determination of samples withdrawn) has finished, the reaction mixture is drawn off after cooling and the reaction products are isolated by separation by settling, optionally followed by extraction of the aqueous layer using an appropriate solvent, such as, for example, the abovementioned water-immiscible solvents.

The aqueous catalytic solution can then be recycled in a fresh reaction for the hydrocyanation of organic compounds containing at least one ethylenic double bond.

Within the context of a continuous implementation of the process, only the organic phase can be drawn off, whereas the aqueous catalytic phase remains in the reactor.

This reaction in two-phase medium makes it extremely simple to implement an industrial process. The ready separation of all the catalyst, on the one hand, and of the reaction products, on the other hand, renders unnecessary a large number of operations, such as distillation of reactants and reaction products or liquid/liquid extraction using an appropriate solvent.

An improvement to the process for the hydrocyanation of compounds containing ethylenic unsaturation according to the present invention relates to the hydrocyanation of the said compounds containing ethylenic unsaturation by reaction with hydrogen cyanide, characterized in that the reaction is carried out in the presence of an aqueous solution of a catalyst comprising at least one transition metal compound, at least one water-soluble phosphine of formula (I) or (II) and a cocatalyst comprising at least one Lewis acid.

The compounds containing ethylenic unsaturation which can be employed in this improvement are generally those which have been mentioned with respect to the base process. However, it is more particularly advantageous to apply it to aliphatic nitriles containing ethylenic unsaturation, in particular to linear pentenenitriles, such as 3-pentenenitrile, 4-pentenenitrile and their mixtures.

These pentenenitriles can contain amounts, generally minor, of other compounds, such as 2-methyl-3-butenenitrile, 2-methyl-2-butenenitrile, 2-pentenenitrile, valeronitrile, adiponitrile, 2-methylglutaronitrile, 2-ethylsuccinonitrile or butadiene, originating from the prior hydrocyanation reaction of butadiene and/or from the isomerization of 2-methyl-3-butenenitrile to pentenenitriles.

The water-soluble phosphines, the transition metal compounds, the operating conditions and the composition of the reaction mixture are the same as for the general hydrocyanation process according to the invention which has been described above but the reaction is additionally carried out in the presence of a Lewis acid.

The Lewis acid used as cocatalyst makes it possible in particular, in the case of the hydrocyanation of aliphatic nitriles containing ethylenic unsaturation, to improve the linearity of the dinitriles obtained, that is to say the percentage of linear dinitrile with respect to all the dinitriles formed, and/or to increase the lifetime of the catalyst.

Lewis acid is understood to mean in the present text, according to the usual definition, compounds which are electron-pair acceptors.

The Lewis acids cited in the work edited by G. A. Olah, "Friedel-Crafts and Related Reactions", volume I, pages 191 to 197 (1963), can in particular be employed.

The Lewis acids which can be employed as cocatalysts in the present process are chosen from compounds of the elements from groups Ib, IIb, IIIa, IIIb, IVa, IVb, Va, Vb, VIb, VIIb and VIII of the Periodic Classification of the Elements, insofar as the said compounds are at least partially soluble and stable in water. These compounds are most often salts, in particular halides, preferably chlorides and bromides, sulphates, carboxylates and phosphates.

Mention may be made, as non-limiting examples of such Lewis acids, of zinc chloride, zinc bromide, zinc iodide, manganese chloride., manganese bromide, cadmium chloride, cadmium bromide, stannous chloride, stannous bromide, stannous sulphate, stannous tartrate, chlorides or bromides of rare-earth metal elements, such as lanthanum, cerium, praseodymium, neodymium, samarium, europium, gadolinium, terbium, dysprosium, holmium, erbium, thulium, ytterbium and lutetium, cobalt chloride, ferrous chloride or yttrium chloride.

It is, of course, possible to employ mixtures of a number of Lewis acids.

It is also advantageous, if appropriate, to stabilize the Lewis acid in aqueous solution by the addition of an alkali metal chloride, such as lithium chloride or sodium chloride in particular. The lithium chloride or sodium chloride/Lewis acid molar ratio varies very widely, for example from 0 to 100, it being possible for the specific ratio to be adjusted depending on the stability of the Lewis acid in water.

Among the Lewis acids, zinc chloride, zinc bromide, stannous chloride, stannous bromide, stannous chloride stabilized with lithium chloride, stannous chloride stabilized with sodium chloride and zinc chloride/stannous chloride mixtures are very particularly preferred.

The Lewis acid cocatalyst employed generally represents from 0.01 to 50 mol per mole of transition metal compound, more particularly of nickel compound, and preferably from 1 to 10 mol per mole.

As for the implementation of the base process of the invention, the catalytic solution used for the hydrocyanation in the presence of Lewis acid can be prepared before it is introduced into the reaction region, for example by addition, to the aqueous solution of the water-soluble phosphine of formula (I) or (II), of the appropriate amount of chosen transition metal compound, of Lewis acid and optionally of the reducing agent. It is also possible to prepare the catalytic solution "in situ" by simple mixing of these various constituents.

The separation of the catalyst in the aqueous phase is easy by simple separation by settling, as has been indicated above for the base process. This aqueous solution of catalyst can thus be recycled in a fresh hydrocyanation reaction. In the case, which is very important economically, of the hydrocyanation of pentenenitriles, it is possible to recycle this catalyst solution either in a fresh hydrocyanation of pentenenitriles or, more generally, in the hydrocyanation of butadiene, resulting in pentenenitriles which are subsequently hydrocyanated with the same catalyst.

It is also possible, under the conditions of the hydrocyanation process of the present invention, and in particular by carrying out the reaction in the presence of the catalyst described above containing at least one water-soluble phosphine of formula (I) or (II) and at least one transition metal compound, to isomerize 2-methyl-3-butenenitrile to pentenenitriles in the absence of hydrogen cyanide.

The 2-methyl-3-butenenitrile subjected to the isomerization according to the invention can be employed alone or as a mixture with other compounds.

Thus, it is possible to use 2-methyl-3-butenenitrile as a mixture with 2-methyl-2-butenenitrile, 4-pentenenitrile, 3-pentenenitrile, 2-pentenenitrile, butadiene, adiponitrile, 2-methylglutaronitrile, 2-ethylsuccinonitrile or valeronitrile.

Thus, it is particularly advantageous to treat the reaction mixture originating from the hydrocyanation of butadiene with HCN in the presence of an aqueous solution of at least one water-soluble phosphine of formula (I) or (II) and of at least one transition metal compound, more preferentially of a nickel compound in the 0 oxidation state, as defined above.

Within the context of this preferred alternative form, as the catalytic system is already present for the hydrocyanation reaction of butadiene, it is sufficient to stop any introduction of hydrogen cyanide in order to allow the isomerization reaction to take place.

It is possible, if appropriate, in this alternative form, to gently sweep the reactor using an inert gas, such as nitrogen or argon, for example, in order to drive off the hydrocyanic acid which could still be present.

The isomerization reaction is generally carried out at a temperature from 10° C. to 200° C. and preferably from 60° C. to 120° C.

In the preferred case of an isomerization immediately following the hydrocyanation reaction of butadiene, it will be advantageous to carry out the isomerization at the temperature at which the hydrocyanation has been carried out.

As for the process for the hydrocyanation of compounds containing ethylenic unsaturation, the catalytic solution used for the isomerization can be prepared before it is introduced into the reaction region, for example by addition, to the aqueous solution of the water-soluble phosphine of formula (I) or (II), of the appropriate amount of chosen transition metal compound and optionally of the reducing agent. It is also possible to prepare the catalytic solution "in situ", by simple mixing of these various constituents. The amount of transition metal compound, and more particularly of nickel, used and the amount of water-soluble phosphine of formula (I) or (II) are the same as for the hydrocyanation reaction.

Although the isomerization reaction is generally carried out without a third solvent, it can be advantageous to add an inert water-immiscible organic solvent which can be that of the subsequent extraction. This is in particular the case when such a solvent has been employed in the hydrocyanation reaction of butadiene which has been used to prepare the mixture subjected to the isomerization reaction. Such solvents can be chosen from those which have been mentioned above for the hydrocyanation.

At the end of the reaction, it is very easy to separate the catalyst from the isomerization reaction products, as has been indicated for the hydrocyanation, and to recycle it, if appropriate, in one of the hydrocyanation reactions described above or in a fresh isomerization reaction.

The following examples illustrate the present invention.

EXAMPLE 1

1) Preparation of the Ni/CBDTSNa$_4$ catalytic solution 50 ml of a solution of 11.3 mmol of sodium salt of 1,2-bis[di(sulphonatophenyl)phosphinomethyl]-cyclobutane (CBDTSNa$_4$) in water are charged to a 100 ml round-bottomed glass flask equipped with a magnetic bar and an ascending reflux condenser; this solution is degassed. 2 g (7.3 mmol) of Ni(cyclooctadiene)$_2$, followed by 35 ml of previously degassed ortho-xylene, are subsequently introduced with stirring and under a stream of argon.

The mixture is heated at 45° C. for 15 h. After cooling, the two-phase system is separated by settling and the aqueous phase, which is highly coloured red, is withdrawn.

Elemental analysis of the aqueous phase reveals an Ni concentration of 8 mmol/100 g and a P concentration of 35.5 mmol/100 g.

2) Hydrocyanation of 3-pentenenitrile 37.4 g of the aqueous solution prepared in 1) are charged to a 150 ml glass reactor stirred using a propeller. The mixture is heated with stirring to 60° C. and then the following are successively injected, while maintaining this temperature:

3.2 ml of an aqueous solution containing 20 mmol of Zn chloride 16.5 g (204 mmol) of 3-pentenenitrile (3PN).

Hydrogen cyanide is then injected at the rate of 1.2 g/h (44 mmol/h) for 0.5 h.

At the end of the test, the reaction mixture obtained is cooled, the possible excess hydrogen cyanide injected is neutralized using a concentrated sodium hydroxide solution and the various constituents are quantitatively determined by gas chromatography (GC).

The following results are obtained:

| | |
|---|---|
| degree of conversion (DC) of 3PN | 7% |
| yield (Yd) of adiponitrile (ADN) with respect to the 3PN converted | 81% |
| Yd of 2-methylglutaronitrile (MGN) with respect to the 3PN converted | 10% |
| Yd of 2-ethylsuccinonitrile (ESN) with respect to the 3PN converted | 1% |
| Yd of valeronitrile (VN) with respect to the 3PN converted | 8% |
| linearity (*) | 89% |
| activity of the catalyst (**) | 4 |
| production efficiency for ADN (with respect to the volume of the aqueous phase) | 65 g/h.1 |

(*) ADN formed/ADN + MGN + ESN formed
(**) number of moles of 3PN converted per mole of Ni employed

EXAMPLE 2

1) Preparation of the Ni/TPPPNa$_6$ catalytic solution 50 ml of a solution of 32.8 mmol of sodium salt of tris(para-phosphophenyl)phosphine (TPPPNa$_6$) in water are charged to a 100 ml round-bottomed glass flask equipped with a magnetic bar and an ascending reflux condenser; this solution is degassed. 2 g (7.3 mmol) of Ni(cyclooctadiene)$_2$, followed by 35 ml of previously degassed ortho-xylene, are subsequently introduced with stirring and under a stream of argon.

The mixture is heated at 45° C. for 15 h. After cooling, the two-phase system is separated by settling and the aqueous phase, which is highly coloured red, is withdrawn.

Elemental analysis of the aqueous phase reveals an Ni concentration of 11.9 mmol/100 g and a P concentration of 216.2 mmol/100 g.

2) Hydrocyanation of 3-pentenenitrile 42.0 g of the aqueous solution prepared in 1) are charged to a 150 ml glass reactor stirred using a propeller. The mixture is heated with stirring to 60° C. and then the following are successively injected, while maintaining this temperature:

3.2 ml of an aqueous solution containing 20 mmol of Zn chloride 23.5 g (290 mmol) of 3-pentenenitrile (3PN).

Hydrogen cyanide is then injected at the rate of 1.8 g/h (67 mmol/h) for 0.6 h.

At the end of the test, the reaction mixture obtained is cooled, the possible excess hydrogen cyanide injected is neutralized using a concentrated sodium hydroxide solution and the various constituents are quantitatively determined by gas chromatography (GC).

The following results are obtained:

| | |
|---|---|
| degree of conversion (DC) of 3PN | 13% |
| yield (Yd) of adiponitrile (ADN) with respect to the 3PN converted | 70% |
| Yd of 2-methylglutaronitrile (MGN) with respect to the 3PN converted | 23% |
| Yd of 2-ethylsuccinonitrile (ESN) with respect to the 3PN converted | 2% |
| Yd of valeronitrile (VN) with respect to the 3PN converted | 4% |
| linearity | 73% |
| activity of the catalyst | 7 |
| production efficiency for ADN (with respect to the volume of the aqueous phase) | 125 g/h.1 |

EXAMPLE 3

1) Preparation of the Ni/DSPCPPNa$_3$ catalytic solution 50 ml of a solution of 32.8 mmol of sodium salt of bis(meta-sulphophenyl)(para-carboxyphenyl)-phosphine (DSPCPPNa$_3$) in water are charged to a 100 ml round-bottomed glass flask equipped with a magnetic bar and an ascending reflux condenser; this solution is degassed. 2 g (7.3 mmol) of Ni(cyclooctadiene)$_2$, followed by 35 ml of previously degassed ortho-xylene, are subsequently introduced with stirring and under a stream of argon.

The mixture is heated at 45° C. for 15 h. After cooling, the two-phase system is separated by settling and the aqueous phase, which is highly coloured red, is withdrawn.

Elemental analysis of the aqueous phase reveals an Ni concentration of 12 mmol/100 g and a P concentration of 53.9 mmol/100 g.

2) Hydrocyanation of 3-pentenenitrile 41.7 g of the aqueous solution prepared in 1) are charged to a 150 ml glass reactor stirred using a propeller. The mixture is heated with stirring to 60° C. and then the following are successively injected, while maintaining this temperature:

3.2 ml of an aqueous solution containing 20 mmol of Zn chloride 23.5 g (290 mmol) of 3-pentenenitrile (3PN).

Hydrogen cyanide is then injected at the rate of 1.8 g/h (67 mmol/h) for 0.75 h.

At the end of the test, the reaction mixture obtained is cooled, the possible excess hydrogen cyanide injected is neutralized using a concentrated sodium hydroxide solution and the various constituents are quantitatively determined by gas chromatography (GC).

The following results are obtained:

| | |
|---|---|
| degree of conversion (DC) of 3PN | 19% |
| yield (Yd) of adiponitrile (ADN) with respect to the 3PN converted | 71% |
| Yd of 2-methylglutaronitrile (MGN) with respect to the 3PN converted | 20% |
| Yd of 2-ethylsuccinonitrile (ESN) with respect to the 3PN converted | 3% |
| Yd of valeronitrile (VN) with respect to the 3PN converted | 6% |
| linearity | 76% |
| activity of the catalyst | 10 |
| production efficiency for ADN (with respect to the volume of the aqueous phase) | 150 g/h.1 |

EXAMPLE 4

1) Preparation of the Ni/DSPSEPNa$_3$ catalytic solution 50 ml of a solution of 32.8 mmol of sodium salt of bis(meta-sulphophenyl)(2-sulphoethyl)phosphine (DSPSEPNa$_3$) in water are charged to a 100 ml round-bottomed glass flask equipped with a magnetic bar and an ascending reflux condenser; this solution is degassed. 2 g (7.3 mmol) of Ni(cyclooctadiene)$_2$, followed by 35 ml of previously degassed ortho-xylene, are subsequently introduced with stirring and under a stream of argon.

The mixture is heated at 45° C. for 15 h. After cooling, the two-phase system is separated by settling and the aqueous phase, which is highly coloured red, is withdrawn.

Elemental analysis of the aqueous phase reveals an Ni concentration of 11.8 mmol/100 g and a P concentration of 54.5 mmol/100 g.

2) Hydrocyanation of 3-pentenenitrile 42.4 g of the aqueous solution prepared in 1) are charged to a 150 ml glass reactor stirred using a propeller. The mixture is heated with stirring to 60° C. and then the following are successively injected, while maintaining this temperature:

3.2 ml of an aqueous solution containing 20 mmol of Zn chloride 23.5 g (290 mmol) of 3-pentenenitrile (3PN).

Hydrogen cyanide is then injected at the rate of 1.8 g/h (67 mmol/h) for 0.5 h.

At the end of the test, the reaction mixture obtained is cooled, the possible excess hydrogen cyanide injected is neutralized using a concentrated sodium hydroxide solution and the various constituents are quantitatively determined by gas chromatography (GC).

The following results are obtained:

| | |
|---|---|
| degree of conversion (DC) of 3PN | 8% |
| yield (Yd) of adiponitrile (ADN) with respect to the 3PN converted | 69% |
| Yd of 2-methylglutaronitrile (MGN) with respect to the 3PN converted | 24% |
| Yd of 2-ethylsuccinonitrile (ESN) with respect to the 3PN converted | 3% |
| Yd of valeronitrile (VN) with respect to the 3PN converted | 4% |
| linearity | 72% |
| activity of the catalyst | 4 |
| production efficiency for ADN (with respect to the volume of the aqueous phase) | 90 g/h.1 |

COMPARATIVE TEST

1) Preparation of the Ni/TPPTSNa$_3$ catalytic solution 500 ml of a solution of 300 mmol of sodium salt of tris(meta-sulphophenyl)phosphine (TPPTSNa$_3$) in water are charged to a 1000 ml round-bottomed glass flask equipped with a stirrer and an ascending reflux condenser; this solution is degassed. 20 g (73 mmol) of Ni(cyclooctadiene)$_2$, followed by 350 ml of previously degassed ortho-xylene, are subsequently introduced with stirring and under a stream of argon.

The mixture is heated at 45° C. for 15 h. After cooling, the two-phase system is separated by settling and the aqueous phase, which is highly coloured red, is withdrawn Elemental analysis of the aqueous phase reveals an Ni concentration of 12.0 mmol/100 g and a P concentration of 49.7 mmol/100 g.

2) Hydrocyanation of 3-pentenenitrile 41.7 g of the aqueous solution prepared in 1) are charged to a 150 ml glass reactor stirred using a propeller. The mixture is heated with stirring to 60° C. and then the following are successively injected, while maintaining this temperature:

3.2 ml of an aqueous solution containing 20 mmol of Zn chloride 8 g (105 mmol) of 3-pentenenitrile (3PN).

Hydrogen cyanide is then injected at the rate of 1.8 g/h (67 mmol/h) for 2 h.

At the end of the test, the reaction mixture obtained is cooled, the possible excess hydrogen cyanide injected is neutralized using a concentrated sodium hydroxide solution and the various constituents are quantitatively determined by gas chromatography (GC).

The following results are obtained:

| | |
|---|---|
| degree of conversion (DC) of 3PN | 89% |
| yield (Yd) of adiponitrile (ADN) with respect to the 3PN converted | 66% |
| Yd of 2-methylglutaronitrile (MGN) with respect to the 3PN converted | 26% |
| Yd of 2 ethylsuccinonitrile (ESN) with respect to the 3PN converted | 5% |
| Yd of valeronitrile (VN) with respect to the 3PN converted | 3% |
| linearity | 68% |
| activity of the catalyst | 20 |
| production efficiency for ADN (with respect to the volume of the aqueous phase) | 90 g/h.1 |

We claim:

1. A process for the hydrocyanation of organic compounds containing at least one ethylenic double bond, said process comprising reacting an organic compound containing at least one ethylenic double bond, at least one compound of a transition metal and at least one water-soluble phosphine with hydrogen cyanide in the presence of an aqueous solution of a catalyst wherein said water-soluble phosphine is a monodentate or bidentate phosphine corresponding to the general formula (I):

wherein:

Ar1 and Ar2, which are identical or different, represent aryl groups or aryl groups containing one or a number of substituents consisting of:
alkyl or alkoxy radical having 1 to 4 carbon atoms, halogen atom, or
hydrophilic group, consisting of:
—COOM, —SO$_3$M or —PO$_3$M, M representing an inorganic or organic cationic residue chosen from a proton, cations derived from alkali or alkaline-earth metals, ammonium cations —N(R)$_4$, in the formula of which the R symbols, which are identical or different, represent a hydrogen atom or an alkyl radical having from 1 to 4 carbon atoms, and other cations derived from metals, the arylcarboxylic acid, arylsulphonic acid or arylphosphonic acid salts of which are soluble in water, Ar3 represents an aryl group containing one or a number of substituents consisting of:
alkyl or alkoxy radical having 1 to 4 carbon atoms, halogen atom,
hydrophilic group, consisting of:
—COOM or —PO$_3$M, M representing an inorganic or organic cationic residue chosen from a proton, cations derived from alkali or alkaline-earth metals, ammonium cations —N(R)$_4$, in the formula of which the R symbols, which are identical or different, represent a hydrogen atom or an alkyl radical having from 1 to 4 carbon atoms, and other cations derived from metals, the arylcarboxylic acid or arylphosphonic acid salts of which are soluble in water,
—N(R)$_3$, in the formula of which the R symbols, which are identical or different, represent a hydrogen atom or an alkyl radical having from 1 to 4 carbon atoms,
—OH,
at least one of the said substituents or Ar3 being a hydrophilic group as defined above, a represents 0 or 1, b represents 0 or 1, c represents an integer from 0 to 3, D represents an alkyl group, a cycloalkyl group or an alkyl or cycloalkyl group containing one or a number of substituents, consisting of:
alkoxy radical having 1 to 4 carbon atoms, halogen atom,
hydrophilic group, consisting of:
—COOM, —SO$_3$M or —PO$_3$M, M representing an inorganic or organic cationic residue chosen from a proton, cations derived from alkali or alkaline-earth metals, ammonium cations —N(R)$_4$, in the formula of which the R symbols, which are identical or different, represent a hydrogen atom or an alkyl radical having from 1 to 4 carbon atoms, and other cations derived from metals, the arylcarboxylic acid, arylsulphonic acid or arylphosphonic acid salts of which are soluble in water,
—N(R)$_3$, in the formula of which the R symbols, which are identical or different, represent a hydrogen atom or an alkyl radical having from 1 to 4 carbon atoms, d represents an integer from 0 to 3, the sum (a+b+c+d) is equal to 3 or to the general formula (II):

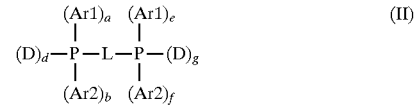

in which:

Ar1, Ar2 and D have the meanings indicated above for the formula (I), a, b, e and f each represent 0 or 1, d and g each represent an integer from 0 to 2, the sum (a+b+d) is equal to 2, the sum (e+f+g) is equal to 2, L represents a single valency bond or a divalent hydrocarbon radical.

2. The process according to claim 1, wherein the water-soluble phosphines are the phosphines of formula (1) or of formula (II) in which Ar1 and Ar2 are phenyl groups or phenyl groups containing one or two substituents, Ar3 is a phenyl group containing one or two substituents, D is an alkyl group having from 1 to 6 carbon atoms, a cycloalkyl group having 5 to 8 carbon atoms, an alkyl group having from 1 to 6 carbon atoms containing one or a number of substituents or a cycloalkyl group having 5 to 8 carbon atoms containing one or a number of substituents and L is a single valency bond, an alkylene radical having from 1 to 6 carbon atoms, a monocyclic or bicyclic cycloalkylene radical having from 4 to 12 carbon atoms, a phenylene radical, a diphenylene radical or a radical deriving from a heterocycle containing one or two oxygen, nitrogen or sulphur atoms in the ring, these various cyclic radicals being bonded directly to one of the phosphorus atoms or to both phosphorus atoms or being bonded to one of the phosphorus atoms or to both via a linear or branched alkylene radical having from 1 to 4 carbon atoms, it being possible for the ring or rings which are optionally part of the divalent radical L to contain one or a number of substituents.

3. The process according to claim 1, wherein the water-soluble phosphines are the phosphines of formula (1) or of formula (II) in which:

the substituent or substituents of Ar1 and Ar2, which are identical or different, represent groups consisting of:

alkyl or alkoxy radical having 1 to 2 carbon atoms, chlorine atom, hydrophilic group, consisting of:

—COOM, —SO$_3$M or —PO$_3$M, M representing an inorganic or organic cationic residue chosen from a proton, cations derived from sodium, potassium, calcium or barium, ammonium, tetramethylammonium, tetraethylammonium, tetrapropylammonium or tetrabutylammonium cations and cations derived from zinc, lead or tin, —N(R)$_3$, in the formula of which the R symbols, which are identical or different, represent a hydrogen atom or an alkyl radical having from 1 to 4 carbon atoms,

—OH the substituent or substituents of Ar3, which are identical or different, represent groups consisting of:

alkyl or alkoxy radical having 1 to 2 carbon atoms, chlorine atom, hydrophilic group, consisting of:

—COOM or —PO$_3$M, M representing an inorganic or organic cationic residue chosen from a proton, cations derived from sodium, potassium, calcium or barium, ammonium, tetramethylammonium, tetraethylammonium, tetrapropylammonium or tetrabutylammonium cations and cations derived from zinc, lead or tin, overall at least two of the said substituents of Ar1, Ar2, Ar3 and D, for the phosphines of formula (I), and of Ar1, Ar2 and D, for the phosphines of formula (II), comprise a hydrophilic group.

4. The process according to claim 1, wherein the transition metal compounds are selected from the compounds consisting of nickel, palladium and iron which are soluble in water or capable of dissolving under the reaction conditions.

5. The process according to claim 1, wherein the transition metal compound is selected from the group consisting of:

a compound wherein nickel is in the zero oxidation state comprising potassium tetracyanonickelate K$_4$[Ni(CN)$_4$], bis(acrylonitrile)nickel(O), bis(1,5-cyclooctadiene) nickel and derivatives containing ligands from group Va; and a nickel compound comprising carboxylates, carbonate, bicarbonate, borate, bromide, chloride, citrate, thiocyanate, cyanide, formate, hydroxide, hydrophosphite, phosphite, phosphate and derivatives, iodide, nitrate, sulphate, sulphite, arylsulphonates and alkylsulphonates.

6. The process according to claim 1, wherein the organic compound containing at least one ethylenic double bond is selected from the group of diolefins consisting of butadiene, isoprene, 1,5-hexadiene or 1,5-cyclooctadiene, aliphatic nitriles containing ethylenic unsaturation.

7. The process according to claim 1, wherein the organic compound is linear pentenenitriles consisting of monoolefins.

8. The process according to claim 1, wherein the amount of compound of the transition metal used is chosen so that there is, per liter of reaction solution, between $10^{-4}$ and 1 mol of transition metal employed and in that the amount of water-soluble phosphine of formula (I) or (II) used is selected such that the number of moles of the water-soluble phosphine with respect to 1 mol of transition metal is from 0.5 to 2000.

9. The process according to claim 1, wherein the hydrocanation reaction is carried out at a temperature from 10° C. to 200° C.

10. The process according to claim 1, wherein the reaction is further carried out in the presence of a cocatalyst comprising at least one Lewis acid.

11. The process according to claim 10, wherein the organic compound comprises aliphatic nitrites containing ethylenic unsaturation and mixtures thereof.

12. The process according to claim 11, wherein the aliphatic nitrites are linear pentenenitriles that contain minor amounts of other compounds comprising 2-methyl-3-butenenitrile, 2-methyl-2-butenenitrile, 2-pentene-nitrile, valeronitrile, adiponitrile, 2-methylglutaro-nitrile, 2-ethylsuccinonitrile or butadiene.

13. The process according to claim 10, wherein the Lewis acid employed as cocatalyst is selected from the compounds of the elements from groups Ib, IIb, IIIb, IVa, IVb, Va, Vb, VIb, VIIb and VIII of the Periodic Classification of the Elements, wherein said compounds are at least partially soluble and stable in water.

14. The process according to claim 13, wherein the Lewis acid is selected from the salts consisting of halides, sulphates, carboxylates and phosphates.

15. The process according to claim 13, wherein the Lewis acid is selected from the group consisting of zinc chloride, zinc bromide, zinc iodide, manganese chloride, manganese bromide, cadmium chloride, cadmium bromide, stannous chloride, stannous bromide, stannous sulphate, stannous tartrate, chlorides or bromides of rare-earth metal elements such as lanthanum, cerium, praseodymium, neodymium, samarium, europium, gadolinium, terbium, dysprosium, holmium, erbium, thulium, ytterbium and lutetium, cobalt chloride, ferrous chloride, yttrium chloride and their mixtures.

16. The process according to claim 13, wherein the Lewis acid represents from 0.01 to 50 mol per mole of transition metal compound.

17. The process according to claim 6, wherein the organic compound is butadiene, and wherein said butadiene hydrocyanates to form 2-methyl-3-butenenitrile that is isomerized to pentenenitriles in the absence of hydrogen cyanide, the isomerization being carried out in the presence of the catalyst containing at least one water-soluble phosphine of formula (I) and (II) and at least one transition metal compound.

18. The process according to claim 17, wherein the 2-methyl-3-butenenitrile which is isomerized is used alone or as a mixture with 2-methyl-2-butenenitrile, 4-pentenenitrile, 3-pentenenitrile, 2-pentenenitrile, butadiene, adiponitrile, 2-methylglytaronitrile, 2-ethylsuccinonitrile or valeronitrile.

19. The process according to claim 17, wherein isomerization is carried out at a temperature from 10° C. to 200° C.

20. The process according to claim 17, wherein the isomerization of 2-methyl-3-butenenitrile to pentenenitriles is further carried out in the presence of a cocatalyst comprising at least one Lewis acid.

21. The process of claim 1, wherein said water-soluble phosphine is a monodentate or bidentate phosphine corresponding to the general formula (II) in which L is a divalent hydrocarbon radical selected from the group consisting of an alkylene radical, a cycloalkylene radical, a phenylene radical, a diphenylene radical and a radical derived from a heterocycle containing one or two oxygen, nitrogen or sulphur atoms in the ring, these various cyclic radicals being bonded directly to one of the phosphorus atoms or to both phosphorus atoms or being bonded to one of the phosphorus atoms or to both via a linear or branched alkylene radical having from 1 to 4 carbon atoms, it being possible for the ring or rings which are optionally part of the divalent radical L to contain one or a number or substituents.

* * * * *

UNITED STATES PATENT AND TRADEMARK OFFICE
CERTIFICATE OF CORRECTION

PATENT NO. : 5,856,555
DATED : January 5, 1999
INVENTOR(S) : Huser et al.

It is certified that error appears in the above-indentified patent and that said Letters Patent is hereby corrected as shown below:

Column 13, line 60, after "substituents" insert --selected from the group--;

Column 13, line 62, after "atom," change "or" to --and--;

Column 13, line 63, after "group," insert --wherein said hydrophilic group is selected from the group--;

Column 13, line 64, change "or" to --and--;

Column 14, line 8, after "substituents" insert --selected from the group--;

Column 14, line 10, after "atoms," insert --and--;

Column 14, line 11, after "group," insert --wherein said hydrophilic group is selected from the group--;

Column 14, line 25, after "atoms," insert --and--;

Column 14, line 35, after "substituents," insert --selected from the group--;

UNITED STATES PATENT AND TRADEMARK OFFICE
CERTIFICATE OF CORRECTION

PATENT NO. : 5,856,555  Page 2 of 3
DATED : January 5, 1999
INVENTOR(S) : Huser et al.

It is certified that error appears in the above-indentified patent and that said Letters Patent is hereby corrected as shown below:

Column 14, line 37, after "atom," insert --and--;

Column 14, line 38, after "group," insert --wherein said hydrophilic group is selected from the group--;

Column 14, line 48, after "water," insert --and--;

Column 15, line 28, after "different," change "represent groups" to --are selected from the group--;

Column 15, line 30, after "atoms," insert --and--;

Column 15, line 31, after "group," insert --wherein said hydrophilic group is selected from the group--;

Column 15, line 42, after "atoms," insert --and--;

UNITED STATES PATENT AND TRADEMARK OFFICE
CERTIFICATE OF CORRECTION

PATENT NO. : 5,856,555
DATED : January 5, 1999
INVENTOR(S) : Huser et al.

It is certified that error appears in the above-indentified patent and that said Letters Patent is hereby corrected as shown below:

Column 15, line 45, after "different," change "represent groups" to --are selected-- from the group--;

Column 15, line 47, after "atom," insert --and--;

Column 15, line 48, after "group," insert --wherein said hydrophilic group is selected from the group--;

Column 15, line 49, after "COOM" change "or" to --and--;

Column 15, line 55, after "tin," begin a new paragraph, on line 56 with "overall"; and

Column 16, line 15, after "pentenenitriles" insert --comprising—; and delete "consisting of".

Signed and Sealed this

Seventh Day of December, 1999

*Attest:*

Q. TODD DICKINSON

*Attesting Officer*     *Acting Commissioner of Patents and Trademarks*